United States Patent [19]

Cottingham et al.

[11] 4,029,418
[45] June 14, 1977

[54] PLANT COMPARATOR

[75] Inventors: Hugh V. Cottingham, Upper Montclair; Joseph Scrocco, West Orange, both of N.J.

[73] Assignee: Black Hole Nebula Incorporated, Upper Montclair, N.J.

[22] Filed: Dec. 31, 1975

[21] Appl. No.: 645,757

[52] U.S. Cl. .................. 356/168; 350/30; 356/244

[51] Int. Cl.$^2$ ...................... G01N 21/04

[58] Field of Search ............ 356/168, 244; 350/30, 350/92

[56] References Cited

UNITED STATES PATENTS

| | | | |
|---|---|---|---|
| 3,565,534 | 2/1971 | Chaban | 356/168 |
| 3,580,682 | 5/1971 | Iliescu | 356/168 |
| 3,712,746 | 1/1973 | Bergeron | 350/30 |
| 3,873,212 | 3/1975 | Shell | 356/168 |

FOREIGN PATENTS OR APPLICATIONS 268,172 10/1929 Italy ........................ 350/91

*Primary Examiner*—John K. Corbin
*Assistant Examiner*—Wm. H. Punter
*Attorney, Agent, or Firm*—Blum, Moscovitz, Friedman & Kaplan

[57] ABSTRACT

An optical comparator for facilitating identification of plant parasites is provided. The comparator includes a lens system for defining at least one object plane and a viewing region. The lens system produces a magnified image at the viewing region of a specimen, such as a plant leaf, when the specimen is disposed at the object plane. A support member is provided for supporting the lens system, the support member further defining an opening for positioning the specimen at the object plane. The support member is further adapted to position a light source to direct light on the object plane. The support member is constructed and arranged to position a photographic reference at the object plane and thereby provide a juxtaposed magnified image of a specimen and photographic reference at the viewing region.

6 Claims, 4 Drawing Figures

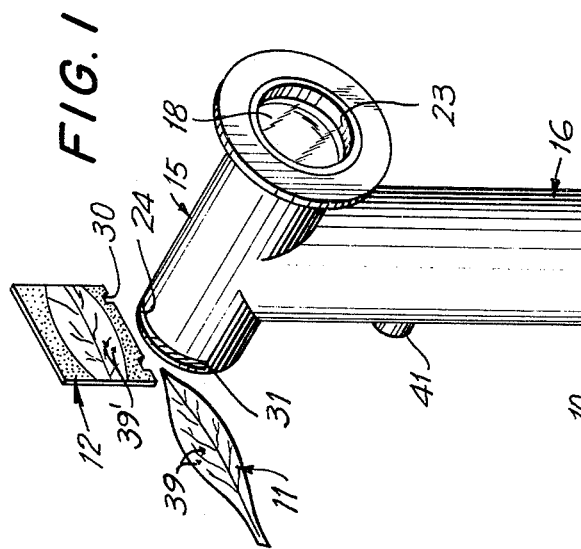
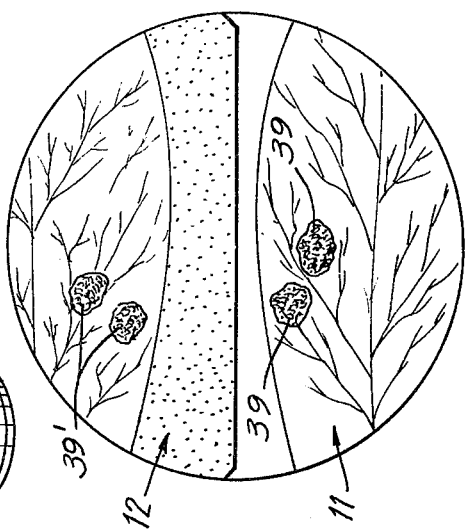
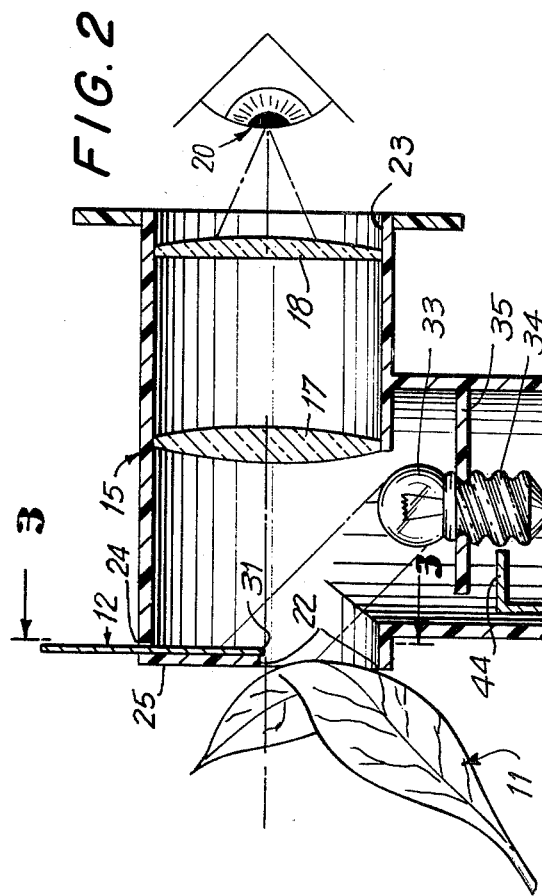
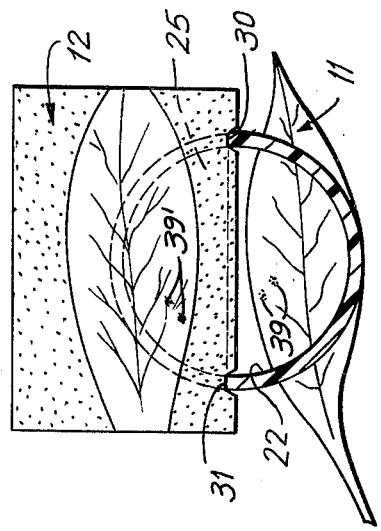
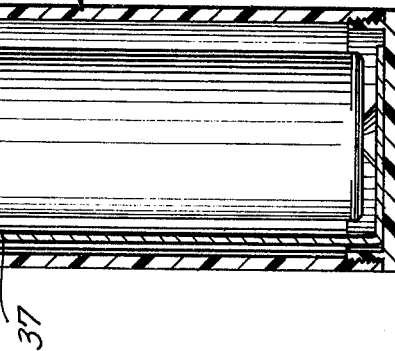

PLANT COMPARATOR

BACKGROUND OF THE INVENTION

This invention is directed to an optical comparator for facilitating identification of plant parasites and in particular to an optical comparator for producing a magnified side-by-side image of a plant specimen and a photographic picture of the plant specimen to facilitate identification of plant parasites afflicting the plant specimen.

Among the difficulties encountered in proper plant care is the inability of the untrained person to identify bugs and other plant parasites that are likely to attack plant life. Such parasites, if unidentified and hence untreated, cause plant illness and ultimately destroy plant life. Although illustrations of the different parasites likely to attack plant life are included in reference texts, heretofore, the manner in which such parasites have been identified have been less than completely satisfactory.

For example, although conventional magnification instrumentation has been utilized to produce a magnified image of the plant specimen, because of the very small size of the plant parasites, as well as their extremely natural looking characteristics, often even under magnification, the plant parasites cannot be discerned, and even if discerned, the specific type of parasite cannot be identified. Although numerous reference texts have been provided, which texts include blown-up black-and-white or color illustrations of the different parasites likely to attack plant life, if such parasites cannot be discerned in the magnified image due to their natural characteristics, the blown-up illustrations are of no help in identifying such parasites. Additionally, when the parasites are illustrated in black-and-white printed illustrations, it is difficult to correlate the parasite that appears in the black-and-white illustration with the magnified multi-colored image of the plant specimen since one of the most distinguishing characteristics of plant parasites is their color or absence of color. Moreover, an enlarged color illustration in a reference text causes certain identifying characteristics of the respective parasites to be over emphasized, thereby providing too much information and thereby distorting in the mind of the user those distinguishing characteristics of the parasites likely to identify same. Finally, textual illustrations of plant parasites usually depict the plant specimen standing alone, instead of illustrating the plant parasite on the plant life afflicted thereby, thus making it difficult for the untrained observer to discern the parasite when the actual plant specimen is studied.

SUMMARY OF THE INVENTION

Generally speaking, in accordance with the invention, an optical comparator for comparing a plant specimen with a comparison photograph of the plant specimen to facilitate identification of plant parasites is provided. The optical comparator includes a lens system defining at least one object plane and a viewing region, the lens system producing a magnified image at the viewing region of the specimen disposed at the object plane. A support member supports the lens system and defines an opening for positioning the specimen at the object plane. A light source is positioned by the support member to direct light on the object plane. The support member is constructed and arranged to releasably secure the photographic reference at the object plane and thereby provide a juxtaposed magnified image of the specimen and photographic reference at the viewing region.

Accordingly, it is an object of this invention to provide an optical comparator for facilitating identification of plant parasites.

A further object of the instant invention is to provide an improved optical comparator for producing a juxtaposed magnified image of a plant specimen and photographic reference of a plant specimen for facilitating comparison thereof.

Still a further object of the instant invention is to provide an improved method for facilitating the identification of plant parasites by using a juxtaposed magnified image of a plant specimen and photographic reference.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of an optical comparator constructed in accordance with a preferred embodiment of the instant invention;

FIG. 2 is a sectional view of the optical comparator illustrated in FIG. 1;

FIG. 3 is a sectional view taken along line 3—3 of FIG. 2; and

FIG. 4 is an illustration of the magnified image produced at the viewing region by the optical comparator depicted in FIG. 1.

DETAILED DESCRIPTION OF THE PREFERRED EMBODIMENT

Reference is now made to FIGS. 1–3 wherein an optical comparator, generally indicated at 10, for facilitating the identification of plant parasites is illustrated. The optical comparator 10 is adapted to produce a magnified side-by-side image of a plant specimen 11 and a photographic reference 12 for facilitating comparison of the plant specimen and photographic reference. For the embodiment depicted in FIGS. 1–3, the photographic reference is formed of a life-size colored photograph of the plant specimen with the parasite to be identified being included in the photograph.

Optical comparator 10 includes a lens support tube 15 and a main support tube 16. At a first end of the lens support tube 15 is a viewing opening 23. The lens support tube 15 includes a semicircular end wall 25 at the other end, which end wall defines a semicircular positioning opening 22.

The lens support tube 15 supports a magnification lens system comprised of first and second lenses 17 and 18, respectively. In the preferred embodiment depicted in FIG. 2, first lens 17 is a double convex lens for providing a magnification by 5X and lens 18 is a single convex lens providing a magnification by 2X. First and second lenses 17 and 18 are respectively positioned by the lens support tube 15 to define a first object plane at the semicircular positioning opening 22 of the lens support tube and to define a viewing region 20, illustrated by the eye in FIG. 2. Accordingly, the lens system produces a magnified semicircular image at the viewing region of a plant specimen positioned in contact with the semicircular positioning opening 22.

A positioning slot 24 for receiving a photographic reference 12 is disposed in lens support tube 15 proximate to the positioning opening 22. The positioning slot 24 is adapted to releasably position a photographic reference 12 substantially flush with the inner surface of end wall 25 and thereby position the photographic reference at the object plane defined by lenses 17 and 18. The photographic reference 12 is a color print photograph depicting a plant specimen to be inspected that is afflicted with a particular parasite. Each photographic reference 12 includes cut-away recesses 30 therein, which recesses are adapted to interfit with the remaining portion 31 of the lens support tube defining the slot 24 and prevent the photographic reference from moving and thereby rendering it more difficult to view a magnified image of same produced by the optical comparator. Accordingly, by inserting a life-size photographic reference 12 into the optical comparator in the manner illustrated in FIG. 3, a semicircular magnified image of the photographic reference is produced at the viewing region.

Main support tube 1 is integrally formed with lens support tube 15 to provide a handle for supporting same and additionally, to position a light bulb 33 for directing light incident upon the object plane to thereby illuminate the plant specimen and photographic reference and insure that a clear lighted image of same is produced at the viewing region. The light bulb 33 includes a threaded conductive base 34, which base is screwed into a receiving wall 35 integrally formed in main tube 16. An elongated resilient conductor 37 is positioned in the main tube 16 to secure a positive electrode 40 of a DC battery 38 in contact with a light bulb contact 39. Additionally, conductor 37 includes an actuating portion 41 projecting through an aperture 42 in the main support tube 16 and a laterally disposed finger 44. By applying pressure to the actuating portion 41 of the conductor 37 projecting from the main tube 16, the finger 44 is brought into contact with the threaded portion of the light bulb 34 and thereby defines a closed circuit with the battery 38 and light bulb 33 to effect a lighting of the light bulb 33. Accordingly, by applying manual pressure to actuating portion 41, light bulb 33 is selectively lit and effects illumination of the plant specimen 11 and photographic reference 12 positioned at the object plane.

It is noted that the light bulb 33 and actuating means therefor could be eliminated and a transparent window could be provided in the support member 15 between the lens 17 and the object plane to direct light upon the object plane. Additionally, the lens support tube 15 could be formed from a clear transparent plastic to thereby provide sufficient light for viewing the juxtaposed magnified image of the plant specimen and photographic reference.

In order to inspect a plant specimen and identify parasites that might be afflicting same, the photographic reference 12 depicting the plant specimen to be studied is inserted into the positioning slot 24. The wall 25 permits the photographic reference to be supported thereagainst and thereby positioned at the object plane to improve the magnified image of same at the viewing region. Thereafter, the plant specimen to be studied is brought into contact with the positioning opening 22 by gently supporting the specimen against the outer surface of the wall 25 thereby placing the plant specimen at the object plane. It is noted that the wall 25 prevents the photographic reference 12 from being distorted or bowed, and thereby displaced from the object plane, when the specimen is brought into contact with the positioning opening 22. It is important that the photographic reference 12 and the specimen 11 be positioned at the object plane in order to guarantee the optical integrity of the magnified image produced at the viewing region.

As illustrated in FIG. 3, the photographic reference 12 includes a plant specimen to be studied, which plant specimen is afflicted by a particular parasite 39'. If the plant specimen 11 is afflicted by a parasite 39, which parasite is the same as the parasite 39' in the photographic reference 12, the magnified side-by-side image produced at the viewing field 20, and depicted in FIG. 4, clearly simplifies identification of the parasite. For example, by including the name of the parasite on the rear side of the photographic reference, once a particular plant parasite is observed and identified, reference can then be made to a text to ascertain how the plant life afflicted by the parasites should be treated. Accordingly, by comparing a specific plant specimen with a series of photographic references of the specific plant specimen including the type of parasites likely to attack such a plant specimen, ready identification of the parasite is achieved.

As noted above, in the embodiments depicted in FIGS. 1–4, a requirement of the photograph 27 is that same be a life-size image in order to provide for the same magnification of the photographic reference as the plant specimen. For the lens system illustrated in FIG. 2, the photograph of the plant specimen could be disposed at a focal plane defined between the lenses 17 and 18, however it would be necessary to enlarge the photographic reference of the plant specimen appropriately larger than the actual specimen in order to insure that the image produced of the photographic reference is proportioned to be life-sized with respect to the plant to be compared. Also, the lens system described herein is presented by way of example, it being realized that other magnification systems could be utilized to obtain the objects of the instant invention.

Additionally, because of their minute size the parasites often appear as small naturally colored or absolutely white dots, which dots are discernible without magnification. Accordingly, a photograph must be utilized in order to provide sufficient resolution to obtain a magnified image of the parasites. Thus, conventional dot printing and imprinting techniques such as offset lithography, thermography, gravure and the like are unable to produce sufficient resolution to permit the photographic minutia to be discerned with the magnified image is produced. Thus the criteria of resolution needed to effect a proper comparison image is obtained by utilizing a photographic reference.

Finally, the slot provided in the tubular support member for positioning the photographic reference is selected to maximize magnification and clarity of the photographic reference image and specimen image for comparison therebetween. Accordingly, the instant invention is characterized by the producing of a juxtaposed magnified image of a plant specimen and photographic reference of the plant specimen with the parasite affliction sought to be discerned for facilitating identification of a plant specimen so afflicted.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:
1. A hand held comparator for comparing a plant specimen to a color photographic reference of a plant specimen afflicted by a predetermined parasite, comprising in combination, lens means defining at least one object plane and a viewing region, said lens means producing a magnified image at the viewing region of a plant specimen disposed at the object plane, a support member defining an enclosure for supporting the lens means, said enclosure being cross-sectioned along a lengthwise extent to define a first opening of said enclosure, said first opening forming a viewing opening proximate to said viewing region defined by said lens means, the other end of said enclosure forming a second opening in substantial optical alignment with said first opening, the second opening in said support member defining an opening for positioning a plant specimen at the object plane, a light source for directing light on the object plane, said support member including positioning means constructed and arranged to position a color photographic reference of a plant specimen afflicted by a predetermined parasite at said object plane to thereby provide a juxtaposed magnified image of said plant specimen and photographic reference at the viewing region.

2. A optical comparator as claimed in claim 1, wherein said color photograph of said plant life is life sized.

3. An optical comparator as claimed in claim 1, wherein said light source includes a light bulb, and means coupled to said light bulb for selectively lighting same to direct light on said object plane during viewing of the magnified juxtaposed image of the specimen and photographic reference.

4. An optical comparator as claimed in claim 1, wherein said positioning means includes a slot in said enclosure, said slot being disposed proximate to said positioning opening to effect disposition of said photographic reference at said object plane.

5. An optical comparator as claimed in claim 4, wherein said enclosure includes an integrally formed end wall at said other end, said end wall defining said positioning opening at said other end of about one-half of the object plane.

6. An optical comparator as claimed in claim 5, wherein the slot formed in said support enclosure is adapted to support a portion of said photographic reference in said enclosure substantially adjacent said end wall.

* * * * *